(12) United States Patent
Kagawa et al.

(10) Patent No.: US 8,303,810 B2
(45) Date of Patent: Nov. 6, 2012

(54) ETHANOL WATER SOLUTION CONCENTRATING DEVICE

(75) Inventors: Kazuhiro Kagawa, Wako (JP); Pu Qian, Wako (JP); Akihisa Tanaka, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 443 days.

(21) Appl. No.: 12/752,037

(22) Filed: Mar. 31, 2010

(65) Prior Publication Data

US 2010/0227390 A1    Sep. 9, 2010

(30) Foreign Application Priority Data

Apr. 3, 2009    (JP) .................................. 2009-091494

(51) Int. Cl.
*B01D 33/70*    (2006.01)

(52) U.S. Cl. ... 210/151; 210/175; 210/258; 210/500.28; 210/500.41

(58) Field of Classification Search .......... 210/150–151, 210/175, 258, 500.28, 500.41
See application file for complete search history.

(56) References Cited

U.S. PATENT DOCUMENTS

2006/0117955 A1* 6/2006 Cranford et al. .................. 96/14
2009/0215139 A1* 8/2009 Datta et al. ..................... 435/162

FOREIGN PATENT DOCUMENTS

JP    2006-136263 A    1/2006
JP    2006-088136 A    6/2006

* cited by examiner

*Primary Examiner* — Chester Barry
(74) *Attorney, Agent, or Firm* — Capitol City TechLaw, PLLC

(57) ABSTRACT

A device for concentrating ethanol from an ethanol water solution yielded from lignocellulose is equipped with a water separation membrane, an ethanol water solution storing unit and a depressurizing container provided so as to sandwich the water separation membrane, a dry gas cylinder for supplying dry gas to an ethanol vapor residing unit above the ethanol water solution storing unit, a pump for sucking in the interior of the ethanol vapor residing unit, and a cold trap for collecting the concentrated ethanol by condensing the ethanol vapor sucked in by the pump.

12 Claims, 2 Drawing Sheets

ETHANOL WATER SOLUTION CONCENTRATING DEVICE

This application claims the foreign priority benefit under 35 U.S.C. §119 of Japanese Patent Application No. 2009-091494 filed on Apr. 3, 2009, the disclosure of which is incorporated herein by reference.

BACKGROUND OF THE INVENTION

1. Field of the Invention

The present invention relates to a device for concentrating an ethanol water solution yielded from ethanol fermentation of a water solution of saccharide generated by saccharification of biomass containing lignocellulose by enzyme.

2. Description of the Related Art

In recent years, from the viewpoint of preventing global warming, it has been called on to reduce emission amount of carbon dioxide which is considered to be one of the reasons of global warming. Therefore, there has been considered to use a mixed fuel of ethanol and a liquid hydrocarbon compound such as gasoline as a vehicle fuel.

The ethanol can be yielded from fermentation of a plant material, for example, an agricultural crop such as sugar cane, corn or the like. Since the plant itself, the raw material of the plant material, has absorbed carbon dioxide via photosynthesis, even though the ethanol produced from the plant material is combusted, the emission amount of carbon dioxide is equal to the amount of carbon dioxide absorbed by the plant itself. In other words, the summed emission amount of carbon dioxide can be made theoretically equal to zero, which is the so-called carbon neutral effect.

However, if sugar cane, corn and the like are consumed in a large amount as the raw materials for preparing ethanol, there is a problem that the amount thereof supplied as food would be decreased. In this regard, there has been considered a technology to produce ethanol by using an inedible biomass containing lignocellulose as a substituent to the plant material such as sugar cane, corn or the like. As examples of the biomass containing lignocellulose, wood, rice straw, haulm, bamboo, pulp and waste materials originated therefrom, such as waste paper, may be given.

As a production method for ethanol, there has been known a method as disclosed in Japanese Patent Laid-Open No. 2006-136263, Japanese Patent Laid-Open No. 2006-88136, in which biomass containing lignocellulose is saccharified by enzyme by adding diastatic enzyme thereto so as to generate saccharide aqueous solution, and further the saccharide aqueous solution is added with ethanol fermentative bacteria to carry out ethanol fermentation, so as to yield ethanol water solution.

However, the ethanol water solution yielded from the above-mentioned ethanol production method is dilute, since the concentration of ethanol is ranged from 0.5 to 5.0 wt %. Therefore, there is a problem that it is difficult to use the same for automotive fuel as it is. Therefore, it is conceivable to concentrate ethanol water solution by separating water therefrom with pervaporation method using an ethanol water solution concentrating device comprising a water separation membrane, an ethanol water solution storing unit which is provided to one surface side of the water separation membrane and which stores the ethanol water solution, and a depressurization unit which is provided to the other surface side of the water separation membrane.

However, in the ethanol water solution concentrating device mentioned above, there is a disadvantage that the ethanol concentration of the concentrated ethanol is still dilute at 3.0 to 5.5 wt %, even after separating a part of water from the ethanol water solution.

SUMMARY OF THE INVENTION

In view of such circumstances, an object of the present invention is to provide a device for concentrating an ethanol water solution yielded from ethanol fermentation of a water solution of saccharide generated by a saccharification of a lignocellulose by enzyme.

In order to achieve the object, the present inventors have given thorough consideration as to the reason why it is not possible to yield concentrated ethanol from the ethanol water solution yielded from ethanol fermentation of the water solution of saccharide generated by the saccharification of the lignocellulose by enzyme by the above-mentioned ethanol water solution concentrating device. As a result the present inventors have found that ethanol vapor evaporated from the ethanol water solution from which a part of water is separated therefrom resides in a space above the liquid level of the ethanol water solution.

The present inventors continued giving consideration on the basis of such findings, and have found that it is possible to yield concentrated ethanol by condensing the ethanol vapor residing in the space above the liquid level of the ethanol water solution, and attained the present invention.

That is, the present invention provides an ethanol water solution concentrating device for concentrating ethanol water solution, including: a water separation membrane; an ethanol water solution storing unit which is provided to one surface side of the water separation membrane, and which stores the ethanol water solution yielded from ethanol fermentation of a water solution of saccharide generated by saccharification of lignocellulose by enzyme; and a depressurization unit provided to the other surface side of the water separation membrane, wherein the device comprises: an ethanol water solution supply unit which supplies the ethanol water solution to the ethanol water solution storing unit; an ethanol vapor residing unit which is provided above the ethanol water solution storing unit and which resides the ethanol vapor; a dry gas supply unit which supplies dry gas to the ethanol vapor residing unit; a suction unit which sucks in the interior of the ethanol vapor residing unit; and an ethanol collection unit which is provided between the ethanol vapor residing unit and the suction unit, and which collects the concentrated ethanol by condensing the ethanol vapor sucked in from the ethanol vapor residing unit.

In the device of the present invention, first, the ethanol water solution is supplied to the ethanol water solution storing unit, by the ethanol water solution supply unit. The ethanol water solution is yielded from ethanol fermentation of the water solution of saccharide generated by the saccharification of lignocellulose by enzyme.

Next, the depressurization unit depressurizes the side of the water separation membrane opposite to the ethanol water solution storing unit. By doing so, the pervaporation method is performed to the ethanol water solution stored in the ethanol water solution storing unit, and a part of water is separated from the ethanol water solution.

On the other hand, the ethanol water solution performed with the pervaporation method has higher ethanol concentration compared to the ethanol water solution before being performed with the pervaporation method, because a part of water is separated therefrom. Therefore, ethanol is easier to evaporate from the ethanol water solution performed with the pervaporation method. As a result, ethanol vapor resides at the ethanol vapor residing unit provided above the ethanol water solution storing unit.

Therefore, in the device of the present invention, the dry gas is supplied to the ethanol vapor residing unit by the dry gas supply unit, and the interior of the ethanol vapor residing unit is sucked in by the suction unit. By doing so, the ethanol vapor residing in the ethanol vapor residing unit is sucked in by the suction unit. At this time, because the dry gas is being supplied to the ethanol vapor residing unit by the dry gas supply unit, the suction unit may continue suction of the ethanol vapor.

Next, the ethanol collection unit collects the concentrated ethanol by condensing the ethanol vapor sucked in. The concentrated ethanol has higher ethanol concentration compared to the ethanol water solution before being performed with the pervaporation method.

Therefore, according to the device of the present invention, it becomes possible to yield concentrated ethanol from the ethanol water solution yielded from ethanol fermentation of the water solution of saccharide generated by the saccharification of the lignocellulose by enzyme.

In the device of the present invention, it is preferable that the device comprise an ethanol water solution circulation unit which takes out the ethanol water solution from the ethanol water solution storing unit, and supplies the same to the ethanol water solution supply unit. By doing so, it becomes possible to prevent lignin and the organic acid contained in the ethanol water solution yielded from ethanol fermentation of the water solution of saccharide generated by the saccharification of the lignocellulose by enzyme from accumulating on the surface of the water separation membrane, and to promote water separation by the water separation membrane.

As a result, the ethanol concentration of the ethanol water solution performed with the pervaporation method is increased, so that the amount of evaporation of the ethanol from the ethanol water solution is increased, and at the same time, the ethanol concentration of the ethanol vapor residing in the space above the liquid level of the ethanol water solution is increased. Thereafter, by condensing the ethanol vapor with higher ethanol concentration, it becomes possible to yield ethanol concentrated to a higher concentration. Therefore, according to the device of the present invention provided with the ethanol water solution circulation unit, it becomes possible to yield ethanol concentrated to a higher concentration from the ethanol water solution yielded from ethanol fermentation of the water solution of saccharide generated by the saccharification of the lignocellulose by enzyme.

Further, in the device of the present invention, a membrane composed of zeolite may be used as the water separation membrane. However, in the pervaporation method using the water separation membrane composed of zeolite, there is a problem that water separation performance of the water separation membrane is deteriorated from organic acid contained in the ethanol water solution yielded from ethanol fermentation of the water solution of saccharide generated by the saccharification of the lignocellulose by enzyme. In this case, it is necessary to adjust pH of the ethanol water solution before performing the pervaporation method, in order to prevent the water separation performance from being deteriorated by the organic acid.

Therefore, in the device of the present invention, as the water separating membrane, a membrane composed of polypyrrole doped with aromatic sulfonated ion or aliphatic sulfonated ion is preferably used in place of membrane composed of zeolite. In the device of the present invention equipped with the water separation membrane composed of polypyrrole, the water separation performance of the water separation membrane is not deteriorated by the organic acid, so that it becomes possible to directly yield concentrated ethanol from the ethanol water solution yielded from ethanol fermentation of the water solution of saccharide generated by the saccharification of the lignocellulose by enzyme without adjusting pH thereof.

DETAILED DESCRIPTION OF THE PREFERRED EMBODIMENTS

Figure 1:
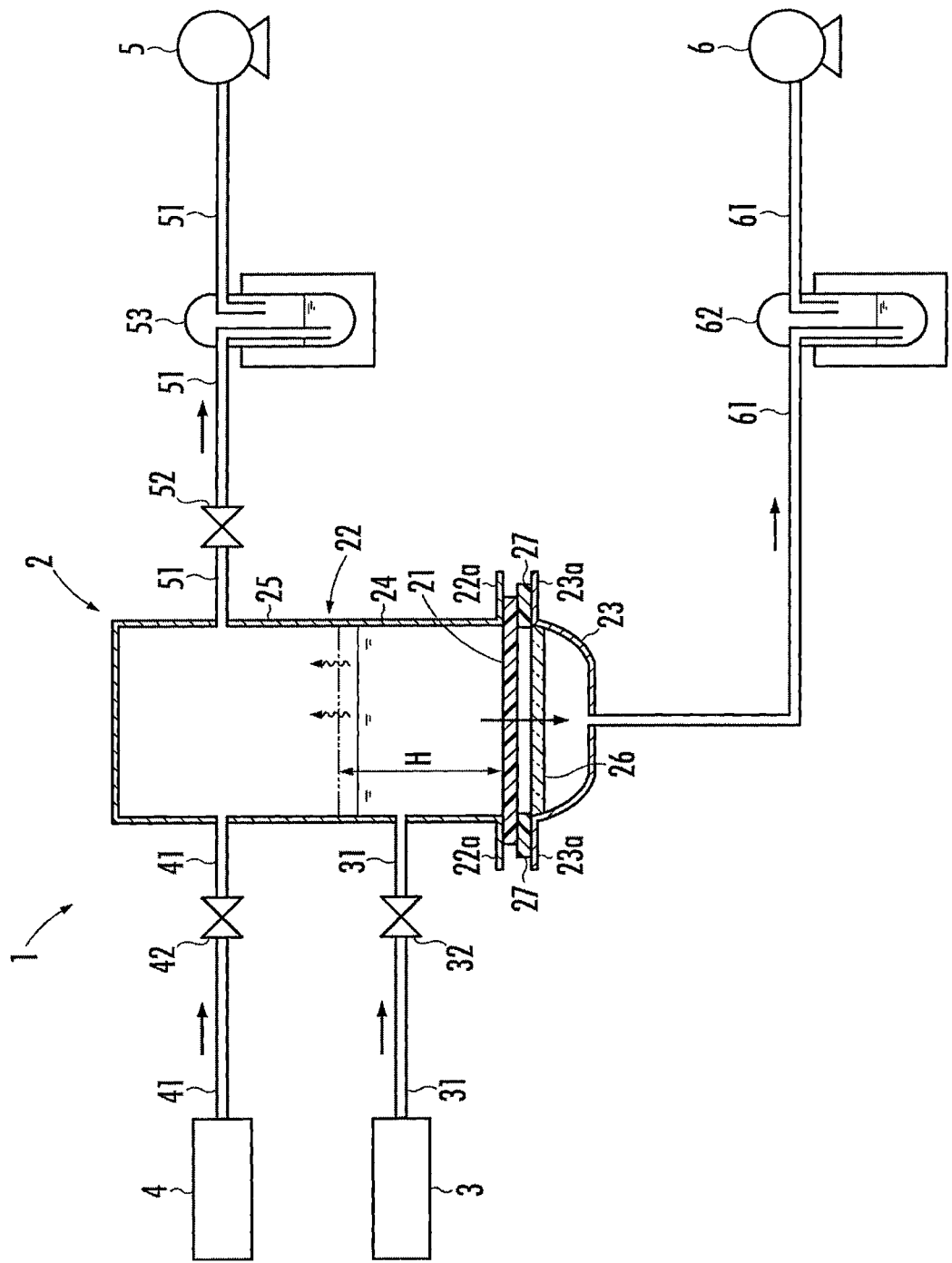
FIG. 1 is an explanatory view of an ethanol water solution concentrating device of the present embodiment.

An embodiment of the present invention will be now described in further detail with reference to the accompanying drawings. An ethanol water solution concentrating device 1 of the present embodiment shown in FIG. 1 is equipped with a pervaporation cell 2, an ethanol water solution retention tank 3, a dry gas cylinder 4, a suction pump 5, and a vacuum pump 6. The pervaporation cell 2 is equipped with a water separation membrane 21, an ethanol water solution container 22 provided to the upper surface side of the water separation membrane 21, and a depressurizing container 23 provided to the lower surface side of the water separation membrane 21.

The water separation membrane 21 is a circular shape having a diameter of 26 mm. As the water separation membrane 21, a membrane composed of polypyrrole doped with aromatic sulfonated ion or with aliphatic sulfonated ion may preferably be used.

As examples of the aromatic sulfonated ion to be doped to polypyrrole, the following substances of chemical formulas (1) to (10) may be given.

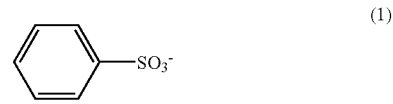

(1)

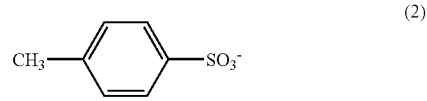

(2)

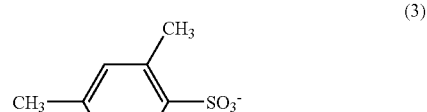

(3)

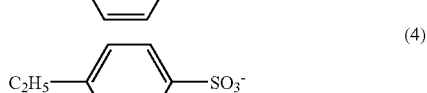

(4)

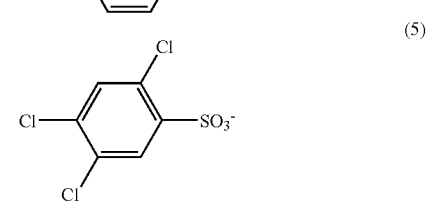

(5)

-continued

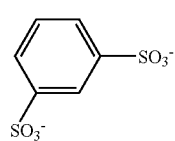
(6)

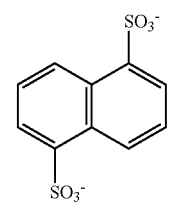
(7)

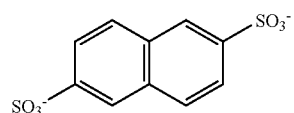
(8)

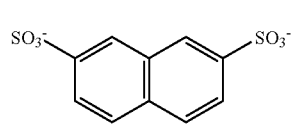
(9)

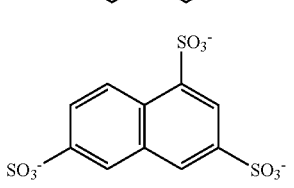
(10)

Further, as examples of the aliphatic sulfonated ion to be doped to polypyrrole, the following substances of chemical formulas (11) and (12), respectively, may be given.

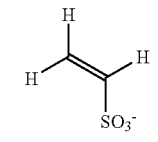
(11)

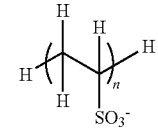
(12)

The water separation membrane 21 used in the present embodiment may be a membrane composed of polypyrrole doped with polyvinyl sulfonated ion, for example.

The ethanol water solution container 22 provided to the upper surface side of the water separation membrane 21 has an inner diameter of 21 mm and a height of 80 mm, and has a tubular body in which lower end thereof is opened and the upper end thereof is closed. The ethanol water solution container 22 is equipped at the outer peripheral surface of the lower end with a flange 22a. An inner circumferential side at the lower side of the ethanol water solution container 22 is exposed with the water separation membrane 21.

The ethanol water solution is stored in the ethanol water solution container 22, and the liquid level thereof is maintained to be equal to or lower than a predetermined height H. Ethanol vapor which evaporated from the ethanol water solution resides above the liquid level of the ethanol water solution. Of the ethanol water solution container 22, the portion below the height H will hereinafter be referred to as an ethanol water solution storing unit 24, and the portion above the height H will be referred to as an ethanol vapor residing unit 25.

The ethanol water solution storing unit 24 is connected to the ethanol water solution retention tank 3 via a first conduit 31. The first conduit 31 is opened to the side surface of the ethanol water solution container 22.

The ethanol vapor residing unit 25 is connected to the dry gas cylinder 4 via a second conduit 41, and is also connected to the suction pump 5 via a third conduit 51. The second conduit 41 is opened to the side surface of the ethanol vapor residing unit 25, and the third conduit 51 is opened to the side opposite to the second conduit 41.

The depressurizing container 23 provided to the lower surface side of the water separation membrane 21 takes an overall funnel shape. The depressurizing container 23 is equipped at the upper end with a circular sintered glass filter (ADVANTEC Ltd., product name: KG-25) 26, and is also equipped at the outer surface side of the upper end with a flange 23a. The sintered glass filter 26 has an effective permeation area of 34.6 mm² (diameter 21 mm).

A sealing member 27 comprised of Parafilm (registered trademark, Alcan Packaging) is provided to the outer circumferential portion of the upper surface side of the sintered glass filter 26. The sealing member 27 is of an annular shape with the outer diameter of 28 mm, and the inner diameter of 21 mm. The water separation membrane 21 is provided at the upper surface side of the sealing member 27.

Further, the depressurizing container 23 is connected to the vacuum pump 6 via a fourth conduit 61. The fourth conduit 61 is opened to the bottom surface of the depressurizing container 23.

The ethanol water solution yielded from ethanol fermentation of the water solution of saccharide generated by the saccharification of the lignocellulose by enzyme is stored in the ethanol water solution retention tank 3. A first on-off valve 32 is provided in the midstream of the first conduit 31 connected to the ethanol water solution retention tank 3. By opening the first on-off valve 32, the ethanol water solution is supplied from the ethanol water solution retention tank 3 to the ethanol water solution storing unit 24.

Dry gas such as dry air, dry nitrogen and the like is stored in the dry gas cylinder 4. A second on-off valve 42 is provided in the midstream of the second conduit 41 connected to the dry gas cylinder 4. By opening the second on-off valve 42, dry gas is supplied from the dry gas cylinder 4 to the ethanol vapor residing unit 25.

The suction pump 5 sucks in the interior of the ethanol vapor residing unit 25 via the third conduit 51. A third on-off valve 52 and a first cold trap 53 are provided in the midstream of the third conduit 51 in this order from the upstream side. The first cold trap 53 condenses the gaseous body sucked in from the ethanol vapor residing unit 25.

The vacuum pump 6 depressurizes the depressurizing container 23 via the fourth conduit 61. A second cold trap 62 is provided in the midstream of the fourth conduit 61. The second cold trap 62 condenses the gaseous body sucked in from the depressurizing container 23.

Next, with reference to FIG. 1, the operation of the ethanol water solution concentrating device 1 of the present embodiment will be explained. First, in the state where the second on-off valve 42 and the third on-off valve 52 are closed, the first on-off valve 32 is opened. By doing so, the ethanol water solution is supplied from the ethanol water solution retention tank 3 to the ethanol water solution storing unit 24. After the liquid level of the ethanol water solution stored in the ethanol water solution storing unit 24 reaches the predetermined height H, the first on-off valve 32 is closed.

Next, the vacuum pump 6 is activated. By doing so, the interior of the depressurizing container 23 is depressurized via the fourth conduit 61. As a result, the pervaporation method is performed to the ethanol water solution stored in the ethanol water solution storing unit 24, and a part of water is separated from the ethanol water solution. The separated water turns into water vapor by permeating through the water separation membrane 21, which is introduced into the second cold trap 62 via the depressurizing container 23 and the fourth conduit 61, and is condensed.

The water separation membrane 21 mainly permeates water contained in the ethanol water solution. However, it also permeates a fraction of ethanol contained in the ethanol water solution. Therefore, a part of the water separated from the ethanol water solution is substantially an ethanol water solution having extremely low ethanol concentration than the ethanol water solution.

On the other hand, the ethanol water solution performed with the pervaporation method has higher ethanol concentration compared to the ethanol water solution before being performed with the pervaporation method, by separating a part of water as the substantial ethanol water solution having extremely low ethanol concentration. As such, ethanol is made easier to evaporate from the ethanol water solution performed with the pervaporation method. As a result, ethanol vapor resides in the ethanol vapor residing unit 25 provided above the liquid level of the ethanol water solution performed with the pervaporation method.

Next, the second on-off valve 42 and the third on-off valve 52 are opened, and the suction pump 5 is activated. By doing so, dry gas is supplied from the dry gas cylinder 4 to the ethanol vapor residing unit 25, and at the same time, a mixed gaseous body of the ethanol vapor inside the ethanol vapor residing unit 25 and dry gas is sucked in by the suction pump 5 and is introduced into the first cold trap 53 via the third conduit 51. Because dry gas is being supplied to the ethanol vapor residing unit 25, the suction pump 5 could continue suction of the mixed gaseous body.

In the first cold trap 53, the ethanol vapor contained in the mixed gaseous body is condensed, and as a result, the concentrated ethanol is collected. The concentrated ethanol has higher ethanol concentration compared to the ethanol water solution before being performed with the pervaporation method.

Therefore, according to the ethanol water solution concentrating device 1 of the present embodiment, it becomes possible to obtain concentrated ethanol from the ethanol water solution yielded from ethanol fermentation of the water solution of saccharide generated by the saccharification of the lignocellulose by enzyme.

Further, in the ethanol water solution concentrating device 1 of the present embodiment, the pervaporation method is performed using the membrane composed of polypyrrole doped with aromatic sulfonated ion or with aliphatic sulfonated ion as the water separation membrane 21. With such water separation membrane 21, upon performing the pervaporation method, water separation performance is not deteriorated by the organic acid contained in the ethanol water solution yielded from ethanol fermentation of the water solution of saccharide generated by the saccharification of the lignocellulose by enzyme.

Therefore, in the ethanol water solution concentrating device 1 of the present embodiment, concentrated ethanol may be directly yielded from the ethanol water solution, without pH adjustment.

Further, in the ethanol water solution concentrating device 1 of the present embodiment, the vacuum pump 6 is activated in the state where the first on-off valve 32 is closed. However, the first on-off valve 32 may be opened. In this case, the amount of supply of ethanol should be adjusted so as to maintain the liquid level of the ethanol water solution stored in the ethanol water solution storing unit 24 at the predetermined height H.

Here, the ethanol water solution yielded from ethanol fermentation of the water solution of saccharide generated by the saccharification of the lignocellulose by enzyme contains lignin and organic acid. In the ethanol water solution storing unit 24, if lignin and organic acid contained in the ethanol water solution accumulates on the upper surface of the water separation membrane 21, water separation performance of the water separation membrane 21 will be deteriorated.

Figure 2:
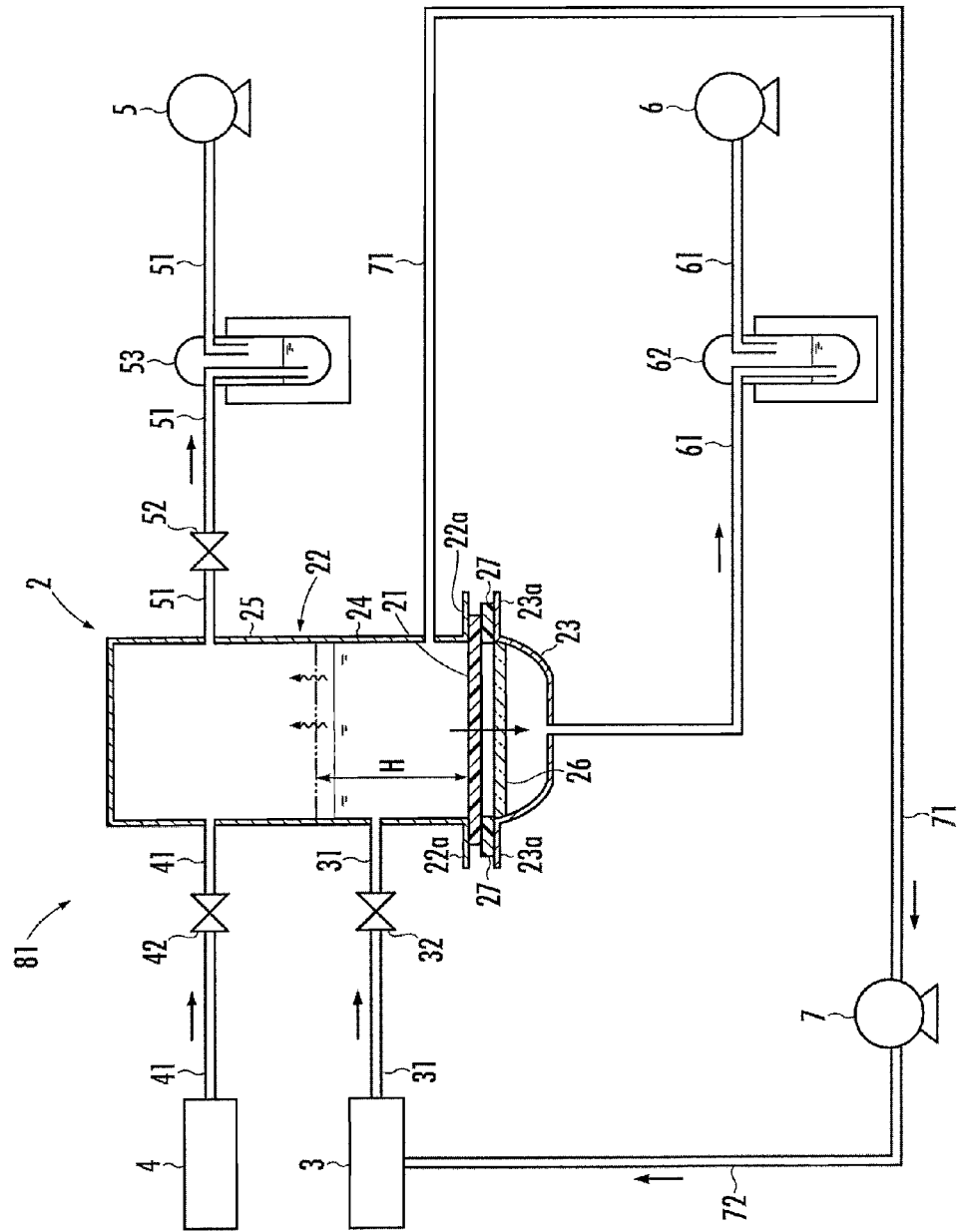
FIG. 2 is an explanatory view of the ethanol water solution concentrating device of the present embodiment equipped with a circulation pump.

Therefore, in the ethanol water solution concentrating device 1 of the present embodiment, it is preferable to further provide a circulation pump 7 shown in FIG. 2. An ethanol water solution concentrating device 81 shown in FIG. 2 has the same configuration with the ethanol water solution concentrating device 1 shown in FIG. 1 except for being provided with the circulation pump 7, a first circulation conduit 71, and a second circulation conduit 72. The circulation pump 7 is connected to the ethanol water solution storing unit 24 via the first circulation conduit 71, and at the same time, connected to the ethanol water solution retention tank 3 via the second circulation conduit 72.

Next, with reference to FIG. 2, the operation of the ethanol water solution concentrating device 81 of the present embodiment will be explained. First, in the state where the second on-off valve 42 and the third on-off valve 52 are closed, the first on-off valve 32 is opened. By doing so, the ethanol water solution is supplied from the ethanol water solution retention tank 3 to the ethanol water solution storing unit 24, exactly the same as in the ethanol water concentration device 1 shown in FIG. 1. After the liquid level of the ethanol water solution stored in the ethanol water solution storing unit 24 reaches the predetermined height H, the first on-off valve 32 is closed.

Next, the vacuum pump 6 is activated. By doing so, the pervaporation method is performed to the ethanol water solution stored in the ethanol water solution storing unit 24, a part of water is separated from the ethanol water solution, and the ethanol vapor evaporated from the ethanol water solution resides in the ethanol vapor residing unit 25, exactly the same as in the ethanol water concentration device 1 shown in FIG. 1.

In the ethanol water solution concentrating device 81, upon activating the vacuum pump 6, the first on-off valve 32 is opened, and at the same time the circulation pump 7 is activated. By doing so, a part of the ethanol water solution stored in the ethanol water solution storing unit 24 is circulated to the ethanol water solution retention tank 3 via the first circulation conduit 71 and the second circulation conduit 72. Further, the ethanol water solution stored in the ethanol water solution retention tank 3 is supplied to the ethanol water solution storing unit 24.

By doing so, the ethanol water solution stored in the ethanol water solution storing unit 24 is circulated and stirred. As a result, lignin and the organic acid contained in the ethanol water solution are prevented from accumulating on the upper surface of the water separation membrane 21, so that water separation by the water separation membrane 21 may be promoted.

Further, as a result of promoting water separation by the water separation membrane 21, the ethanol concentration of the ethanol water solution performed with the pervaporation method is increased, so that the amount of ethanol vapor residing in the ethanol vapor residing unit 25 is increased and the ethanol concentration of the ethanol vapor is increased.

Next, the second on-off valve 42 and the third on-off valve 52 are opened, and the suction pump 5 is activated. By doing so, the mixed gaseous body of the ethanol vapor inside the ethanol vapor residing unit 25 and dry gas is introduced into the first cold trap 53, exactly the same as in the ethanol water solution concentrating device 1. The ethanol vapor contained in the mixed gaseous body is condensed in the first cold trap 53.

In the ethanol water solution concentrating device 81, because the ethanol concentration of the ethanol vapor residing in the ethanol vapor residing unit 25 is increased, it becomes possible to yield ethanol concentrated to a higher concentration, by condensing the ethanol vapor.

Therefore, according to the ethanol water solution concentrating device 81 of the present embodiment equipped with the circulation pump 7, it becomes possible to yield ethanol concentrated to a higher concentration, from the ethanol water solution yielded from ethanol fermentation of the water solution of saccharide generated by the saccharification of the lignocellulose by enzyme.

What is claimed is:

1. An ethanol water solution concentrating device for concentrating ethanol water solution, comprising:
    a water separation membrane;
    an ethanol water solution storing unit which is provided to one surface side of the water separation membrane;
    a depressurization unit provided to the other surface side of the water separation membrane;
    an ethanol water solution supply unit connected to the ethanol water solution storing unit;
    an ethanol vapor residing unit which is provided above the ethanol water solution storing unit;
    a dry gas supply unit connected to the ethanol vapor residing unit;
    a suction unit connected to the ethanol vapor residing unit; and
    an ethanol collection unit which is provided between the ethanol vapor residing unit and the suction unit, and
    wherein the ethanol water solution storing unit stores an ethanol water solution yielded from ethanol fermentation of a water solution of saccharide generated by saccharification of lignocellulose by enzyme,
    the ethanol water solution supply unit supplies the ethanol water solution to the ethanol water solution storing unit,
    the ethanol vapor residing unit provides a space wherein ethanol vapor resides,
    the dry gas supply unit supplies dry gas to the ethanol vapor residing unit,
    the suction unit evacuates the interior of the ethanol vapor residing unit, and
    the ethanol collection unit condenses and collects concentrated ethanol condensed from ethanol vapor evacuated from the ethanol vapor residing unit.

2. The ethanol water solution concentrating device according to claim 1, wherein the depressurization unit comprises
    a depressurizing container provided to the side of the water separation membrane opposite to the ethanol water solution storing unit, and
    a vacuum pump for depressurizing the interior of the depressurizing container.

3. The ethanol water solution concentrating device according to claim 1, wherein the ethanol water solution supply unit comprises
    a first conduit opened to a side surface of the ethanol water solution storing unit, and
    an ethanol water solution retention tank connected to the ethanol water solution storing unit by the first conduit via a first on-off valve.

4. The ethanol water solution concentrating device according to claim 1, wherein the dry gas supply unit comprises
    a second conduit opened to a side surface of the ethanol vapor residing unit, and
    a dry gas cylinder connected to the ethanol vapor residing unit by the second conduit via a second on-off valve.

5. The ethanol water solution concentrating device according to claim 4, wherein the dry gas cylinder retains dry air.

6. The ethanol water solution concentrating device according to claim 4, wherein the dry gas cylinder retains dry nitrogen.

7. The ethanol water solution concentrating device according to claim 1, wherein the suction unit comprises
    a third conduit opened to the side surface of the ethanol vapor residing unit, and
    a suction pump connected to the ethanol vapor residing unit by the third conduit via a third on-off valve, and
    wherein the ethanol collection unit comprises a cold trap provided in the midstream of the third on-off valve and the suction pump.

8. The ethanol water solution concentrating device according to claim 1, further comprising an ethanol water solution circulation unit,
    wherein the circulation unit takes out the ethanol water solution from the ethanol water solution storing unit, and supplies the same to the ethanol water solution supply unit.

9. The ethanol water solution concentrating device according to claim 8, wherein the ethanol water solution circulation unit comprises
    a first circulation conduit opened to a side surface of the ethanol water solution storing unit,
    a circulation pump connected to the first circulation conduit, and
    a second circulation conduit connecting the circulation pump and the ethanol water solution supply unit.

10. The ethanol water solution concentrating device according to claim 1, wherein the water separating membrane comprises polypyrrole doped with aromatic sulfonated ion.

11. The ethanol water solution concentrating device according to claim 1, wherein the water separating membrane comprises polypyrrole doped with aliphatic sulfonated ion.

12. The ethanol water solution concentrating device according to claim 11, wherein the aliphatic sulfonated ion comprises polyvinyl sulfonated ion.

* * * * *